United States Patent [19]
Stolz

[11] Patent Number: 5,938,030
[45] Date of Patent: Aug. 17, 1999

[54] PACKAGING ARRANGEMENT FOR NAIL CORRECTION STRIPS

[75] Inventor: Bernd Stolz, Amberg, Germany

[73] Assignee: Bernd Stolz GmbH, Amberg, Germany

[21] Appl. No.: 08/788,913

[22] Filed: Jan. 22, 1997

[30] Foreign Application Priority Data

Jun. 11, 1996 [DE] Germany .............. 296 10 208

[51] Int. Cl.⁶ .................................. B65D 71/00

[52] U.S. Cl. ........................... 206/438; 206/460

[58] Field of Search .................. 602/6, 22, 31; 506/438, 440, 441, 363, 370, 460

[56] References Cited

U.S. PATENT DOCUMENTS 3,799,160  3/1974  Hahn .

FOREIGN PATENT DOCUMENTS 0 282 645  9/1988  European Pat. Off. .

Primary Examiner—Jacob K. Ackun
Attorney, Agent, or Firm—Browdy and Neimark

[57] ABSTRACT

In a packaging arrangement for nail correction strips, it is provided for simplification of the application that each nail correction strip is arranged on a film- or cardboard-like carrier projecting over the sides of the actual correction strip. Favorably, a spacer strip, on which in turn rests the nail correction strip, is arranged on the carrier.

8 Claims, 1 Drawing Sheet

PACKAGING ARRANGEMENT FOR NAIL CORRECTION STRIPS

BACKGROUND OF THE INVENTION

1. Field of the Invention

The invention relates to a packaging arrangement for nail correction strips.

2. Background Art

Nail correction strips of the generic type are known from the European patent 0 282 645. Nail correction strips of this type are used to straighten out strongly curved and laterally in-grown toe nails and to remove the pain inflicted by the curvature.

For this purpose, plastic strips with a comparably high elastic restoring force have been developed, which are fastened on the surface of the nail to be corrected by means of an instantaneous adhesive and thus transfer the inherently elastic restoring forces onto the nail permanently in such a manner that the edges are straightened out in a direction for the curvature to be corrected.

The handling of instantaneous adhesive requires a high degree of alertness, as due to its great adhesive strength, there is a danger of the fingers of the user being glued together or other damage being caused by the adhesive.

SUMMARY OF THE INVENTION

Proceeding from this, it is the object of the invention to develop a packaging arrangement of the kind mentioned at the outset such that it enables on the one hand space-saving storage and cost-saving shipment, on the other hand, however, also simplified handling in fastening the strip to the nail.

According to the invention, this object is solved by the nail correction strip being arranged on a film- or cardboard-like carrier by far exceeding the size of the actual correction strip especially on the sides.

Due to this design, it is possible to apply the adhesive to the correction strip without the correction strip itself having to be held by the user. Thus, the carrier offers a very simple and convenient possibility of handling. Once the correction strip is provided with adhesive, its side coated with adhesive is applied to the nail. The handling portions of the carrier, which jut out on both sides, allow pressure to be exerted on the correction strip via the carrier and the carrier to be pulled off after having been positioned. The carrier is connected with the correction strip by adhesion or by a pressure-sensitive adhesive of low adhesive strength, thus enabling on the one hand safe handling of the combination of carrier and correction strip, on the other hand, however, guaranteeing that the correction strip stays on the nail after the carrier has been pulled off.

In a further embodiment of the invention it can be provided that the carrier and the correction strip are covered by a covering film which is removed before application.

Favorably it can furthermore be provided that several carriers are combined as a sheet of film or as a sheet of cardboard and that before each use a carrier strip together with a correction strip is detached by way of a perforation or by cutting off.

In a further embodiment of the invention it is provided that on the carrier a spacer strip is arranged, on which in turn rests the nail correction strip. Thus it is achieved that the nail correction strip is located at a distance from the carrier, which substantially simplifies the application without a user's fingers coming in contact with the adhesive.

Favorably, the spacer strip consists of an elastic material, in particular an elastic plastic material.

The nail correction strip is adhesively connected with the spacer strip such that the nail correction strip remains on the nail when being pressed on the nail to be corrected and coated with adhesive, as the adhesive strength between the nail correction strip and the spacer strip is adjusted to be correspondingly low. This adhesive strength can be produced by an adhesive or, for example, by adhesion.

According to a further favorable feature of the invention, the width of the carrier corresponds to the length of the nail correction strip, which is placed thereon. Accordingly, by the aid of the width of the carrier, the handling person can measure on the nail of the patient, whether the length of the nail correction strip intended for use is right and, if necessary, can choose another size of correction strips without having to remove the nail correction strip from the carrier.

Details of the invention will become apparent from the ensuing description of a preferred embodiment, taken in conjunction with the drawing.

DESCRIPTION OF THE PREFERRED EMBODIMENT

Figure 1:
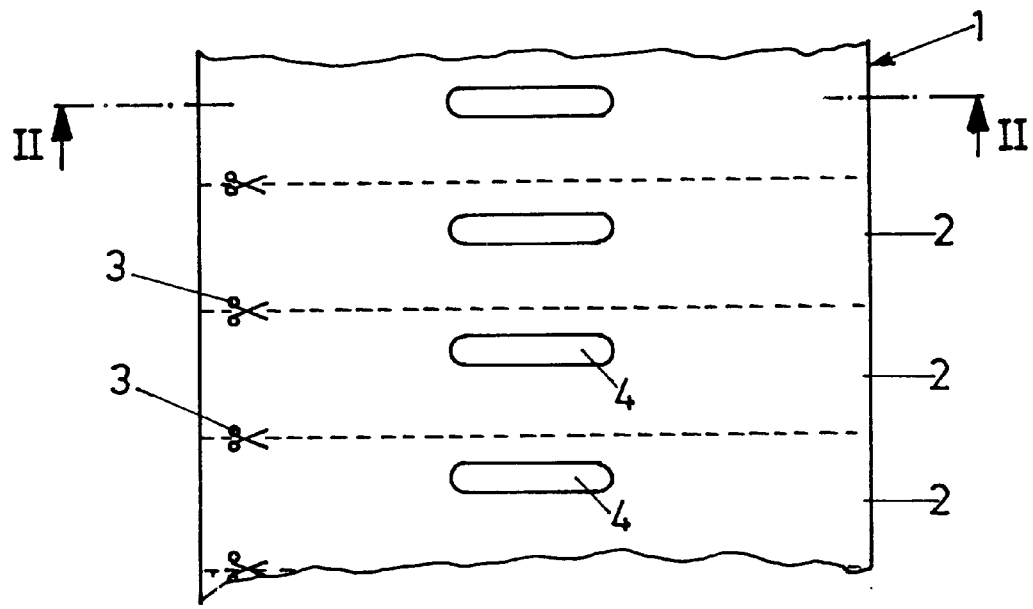
FIG. 1 is a plan view of a carrier unit comprising several carrier strips.
Figure 2:
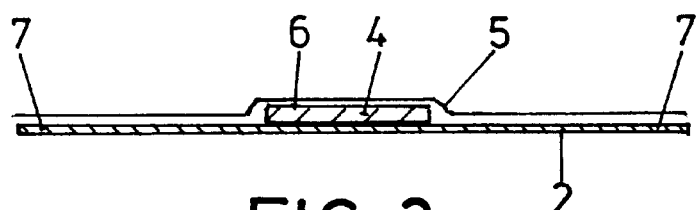
FIG. 2 is a section along the line II—II in FIG. 1.

The drawing shows a carrier unit 1 in the form of a cardboard sheet, said carrier unit comprising several carriers 2, which are connected with each other for the time being and, as is outlined by the symbol 3 of the scissors, can be separated from each other when needed.

A correction strip 4 out of plastic material is disposed on each carrier 2, each carrier 2 and each correction strip 4 being covered by a covering film 5.

In use, a strip-shaped carrier 2 is cut off the carrier unit 1 and the protective film 5 is removed.

An instantaneous adhesive is then applied to the upper side 6 of the correction strip 4 and the user seizes the carrier with both hands at the lateral holding portions 7, turns it over and the presses the coated upper side 6 of the correction strip 4 onto the nail to be corrected. After positioning, the carrier 2 is pulled off and the correction strip 4 rests on the nail without the danger of the handling person coming in contact with the adhesive.

Figure 3:
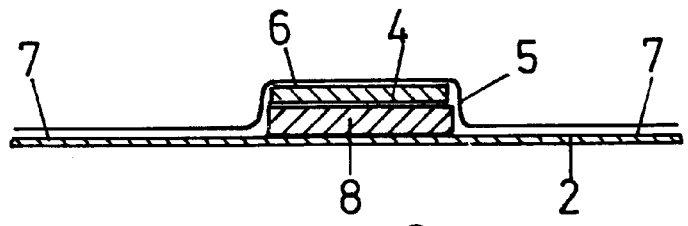
FIG. 3 is a section corresponding to FIG. 2 of a second embodiment.

In the embodiment shown in FIG. 3, between the carrier 2 and the nail correction strip 4, a spacer strip 8 out of plastic material is arranged additionally, ensuring that the nail correction strip 4 projects during application and thus can be glued on more easily without the danger of the handling person coming in contact with the adhesive applied to the nail.

What is claimed is:

1. A packaging arrangement including at least one nail correction strip, said nail correction strip having a elastic restoring force and a side having an instantaneous adhesive which can be glued onto a top of an ingrown toenail, said packaging arrangement comprising, said correction strip (4) arranged on a flat carrier (2) projecting over sides of said correction strip, the correction strip (4) being removably arranged on the carrier (2) by means of a pressure-sensitive adhesive of low adhesive strength which is less than that of said instantaneous adhesive, and wherein when said correction strip is glued to said top of said ingrown toenail and said flat carrier is removed, said elastic restoring force of said connection strip being greater than that of said ingrown toenail so as to lift said ingrown toenail during growth.

2. A packaging arrangement according to claim 1, wherein a plurality of said nail correction strip are arranged on said flat carrier.

3. A packaging arrangement according to claim 1, wherein the carrier (2) and the correction strip (4) are covered by a protective film (5).

4. A packaging arrangement according to claim 1, wherein several carriers (2) are combined as a sheet of film or as a sheet of cardboard and that before each use, a carrier strip together with said correction strip (4) is detachable by way of a perforation or by being cut off.

5. A packaging arrangement according to claim 1, wherein the carrier (2) is provided with a spacer strip (8), on which in turn rests the nail correction strip (4).

6. A packaging arrangement according to claim 5, wherein the spacer strip (8) consists of an elastic material, in particular of an elastic plastic material.

7. A packaging arrangement according to claim 5, wherein the nail correction strip (4) is adhesively connected with the spacer strip (8) such that when pressed on the nail to be corrected and coated with adhesive, the nail correction strip (4) remains on the nail due to the low adjustment of the adhesive strength between the nail correction strip and the spacer strip (8).

8. A packaging arrangement according to claim 1, wherein the width of the carrier (2) corresponds to the length of the nail correction strip (4) arranged thereon.

* * * * *